(12) United States Patent
Richards et al.

(10) Patent No.: US 6,759,011 B1
(45) Date of Patent: Jul. 6, 2004

(54) STACKABLE NON-STICK COVERSLIP

(75) Inventors: William L. Richards, Tucson, AZ (US); Kurt Reinhardt, Tucson, AZ (US); Samuel W. Crouch, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 100 days.

(21) Appl. No.: 09/716,344

(22) Filed: Nov. 20, 2000

Related U.S. Application Data
(60) Provisional application No. 60/166,771, filed on Nov. 22, 1999, and provisional application No. 60/193,797, filed on Mar. 31, 2000.

(51) Int. Cl.[7] .............................................. C12M 1/16
(52) U.S. Cl. ........................ 422/99; 422/104; 436/174; 436/177; 435/288.3; 435/305.3; 435/305.4
(58) Field of Search ........................ 422/99, 101, 102, 422/103, 104; 435/288.3, 288.4, 305.3, 305.4; 436/174, 177

(56) References Cited

U.S. PATENT DOCUMENTS

| | | | |
|---|---|---|---|
| 3,532,412 A | 10/1970 | Miller | 350/95 |
| 3,833,449 A | 9/1974 | Johnson | 156/556 |
| 4,428,793 A | 1/1984 | Sato et al. | 156/285 |
| 4,447,140 A | 5/1984 | Campbell et al. | 350/534 |
| 4,481,246 A | 11/1984 | Melisz et al. | 428/210 |
| 4,790,640 A | 12/1988 | Nason | 350/534 |
| 5,002,736 A | 3/1991 | Babbitt et al. | 422/100 |
| 5,492,837 A | 2/1996 | Naser-Kolahzadeh et al. | 436/176 |
| 5,635,396 A | * 6/1997 | Fedun | 435/283.1 |
| 5,638,459 A | 6/1997 | Rosenlof et al. | 382/133 |
| 5,763,263 A | 6/1998 | Dehlinger | 435/287 |
| 5,827,748 A | * 10/1998 | Golden | 436/527 |
| 5,948,685 A | * 9/1999 | Angros | 422/101 |
| 6,052,224 A | 4/2000 | Richardson | 359/398 |

FOREIGN PATENT DOCUMENTS

| | | | |
|---|---|---|---|
| EP | 0751215 | * | 1/1997 |
| EP | 0 961 109 A2 | | 12/1999 |
| JP | 08254205 | | 9/1996 |
| JP | H11-343740 | | 5/2001 |
| WO | 38848 | * | 5/2001 |

OTHER PUBLICATIONS

Package panel for Tissue–Tek SCA Coverslipping Film, No Date Supplied.

* cited by examiner

*Primary Examiner*—Lyle A. Alexander
(74) *Attorney, Agent, or Firm*—Huw R. Jones; McDonnell Boehnen Hulbert & Berghoff

(57) ABSTRACT

A stackable non-stick coverslip is disclosed and includes a glass plate in combination with a protuberance on the upper surface thereof and/or an adhesive on the bottom surface thereof. The protuberance provides an elevational alternation that defines a supporting plane for an adjacent coverslip. The supporting plane provides a gap between adjacently stacked coverslips, thereby avoiding adherence and sticking. The adhesive secures the coverslip to a glass slide.

12 Claims, 6 Drawing Sheets

STACKABLE NON-STICK COVERSLIP

CROSS REFERENCE

The benefit of U.S. Provisional Application Nos. 60/166,771, filed Nov. 22, 1999, and 60/193,797, filed Mar. 31, 2000, is hereby claimed.

BACKGROUND OF THE INVENTION

The present invention relates generally to new and improved coverslip and more particularly to a stackable non-stick coverslip for use, for example, in an automated coverslipper apparatus or system.

As is well known in the medical art, a tissue specimen, such as a human tissue specimen, is mounted on a conventional glass slide for diagnostic purposes. The glass slide, carrying the tissue section under examination, is subjected to certain reagents and stained in accordance with an established protocol in order to facilitate characterization and diagnosis of the tissue sample. Often the glass slide is "covered" with a chemical coverslip or a glass coverslip to substantially avoid contamination and to permit long-term archiving of the slide.

One presently available glass coverslip has the same configuration as a conventional glass slide, i.e., substantially rectangular. The length and thickness are, by comparison, significantly reduced to decrease production costs. Another available glass coverslip is substantially circular, having a diameter corresponding to the width of a conventional glass slide.

Glass coverslips may be placed upon the tissue-carrying slide manually or by an automated coverslipper. One such automated system is shown in U.S. Pat. No. 3,833,449, and the teachings thereof are incorporated herein by reference. Typically the glass coverslips are vertically stacked in a housing, and an individual coverslip is placed upon the glass slide by either a piston-like mechanism (which pushes the uppermost coverslip in the housing onto the glass slide) or a vacuum mechanism (which lifts the top coverslip for appropriate placement and release).

Moisture between adjacent coverslips in the housing substantially interferes with the covering process and equipment. That is, condensation interposed adjacently stacked coverslips causes adherence, or "sticking," such that more than one coverslip is extracted by a single covering operation. The result is often one or more broken coverslips and a certain amount of "downtime" for maintenance of the system.

For archiving, it is desirable to permanently affix the coverslip to the glass slide. This allows the analyzed specimen to be stored for future reference thereto. Glues are typically used to permanently bond the coverslip to the glass slide, over the stained tissue sample. Such a glue is usually applied manually to either the coverslip or glass slide.

There is a continuing need for an improved coverslip that avoids or overcomes the foregoing deficiences.

SUMMARY OF THE INVENTION

In a principal aspect, the present invention is a stackable non-stick coverslip. In one aspect, the coverslip includes a glass plate and a protuberance on the upper, substantially planar surface thereof. The protuberance provides an elevational alternation that, in cooperation with the glass plate, defines a supporting plane for an adjacent coverslip. The supporting plane is acutely oriented to top surface of the glass plate. In a second aspect, the coverslip includes an adhesive on the lower surface of the glass plate. Upon solvent activation, the adhesive secures, or affixes, the coverslip to a conventional glass slide, thereby covering and protecting the stained tissue sample.

It is thus an object of the present invention to provide a new and improved coverslip. Another object is a stackable coverslip for an automated coverslip applicator, wherein adherence or sticking of adjacently stacked coverslips is substantially avoided. Still another object is a pre-glued stackable coverslip such that the coverslip may be adhered to a glass slide, thereby protecting the analyzed tissue sample. Yet another object of the present invention is a readily and inexpensively manufactured, pre-glued, stackable and non-stick coverslip.

These and other features, objects and advantages of the present invention are set forth or apparent in the following detailed description.

BRIEF DESCRIPTION OF THE DRAWING

Various preferred embodiments of the present invention are described herein with reference to the drawing herein.

DETAILED DESCRIPTION OF VARIOUS PREFERRED EMBODIMENTS

Figure 1:
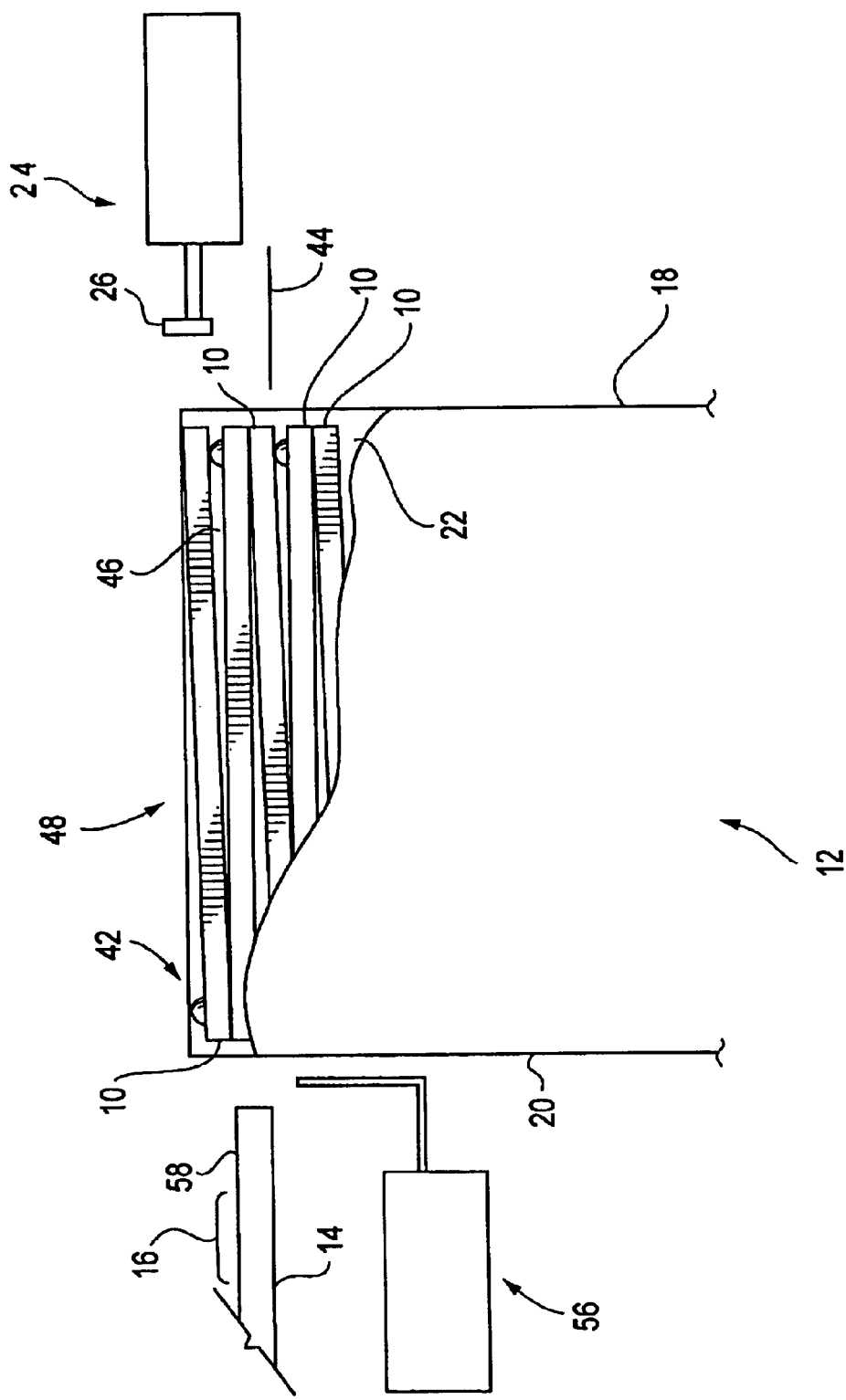
FIG. 1 is a simplified, partial cut-away side view of a coverslipper apparatus for use with the present invention, and illustrating a first preferred embodiment thereof.
Figure 2:
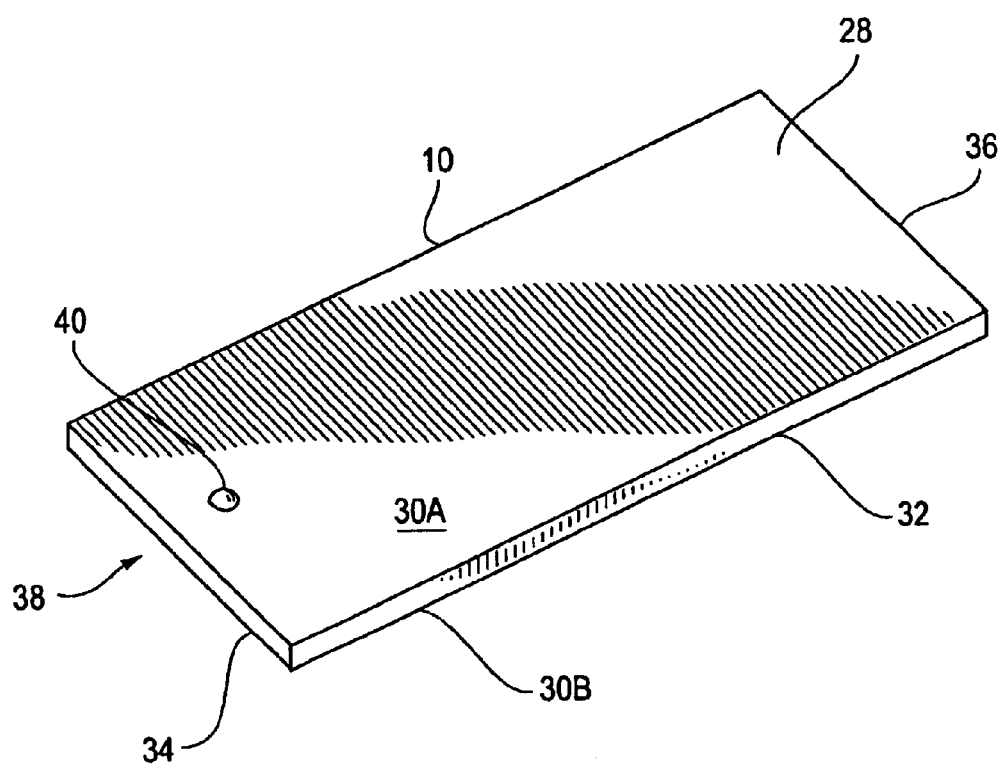
FIG. 2 is a perspective view of the glass coverslip shown in FIG. 1.

With reference to FIGS. 1 and 2, a preferred embodiment of the present invention is shown as a glass coverslip 10 for use in an automated coverslipper, generally designated 12. The coverslipper 12 places the coverslip 10 upon a conventional glass slide 14, having a substantially rectangular configuration and carrying a tissue specimen 16. The coverslip 10 substantially avoids contamination and facilitates processing of the specimen 16.

The coverslipper 12 includes a magazine 18, having an open dispensing end 20, adjacent and facing the glass slide 14. The magazine 18 defines a substantially rectangular chamber 22, wherein the coverslips 10 are stacked in a substantially vertical arrangement. A conventional transfer mechanism, generally designated 24, moves the top, or uppermost, coverslip 10 from the chamber 22, onto the awaiting glass slide 14. For purposes of illustration only, transfer mechanism 24 includes a piston 26, adapted to horizontally engage and "push" the top coverslip 10 in the magazine 18 onto the glass side 14. With each "push," the stack of coverslips 10 advances upwardly in a conventional manner to properly align the next coverslip 10 with respect to the piston 26.

Referring now to FIGS. 1 and 2, the coverslip 10 includes a glass plate 28, having substantially planar top and bottom surfaces 30A, 30B, and a periphery 32. In this preferred embodiment, the glass plate 28 has a substantially rectangular configuration, with a length and a thickness slightly less than the conventional glass slide 14. The plate 28 defines opposed ends 34, 36, respectively, corresponding to the width of the glass slide 14.

Figure 5A:
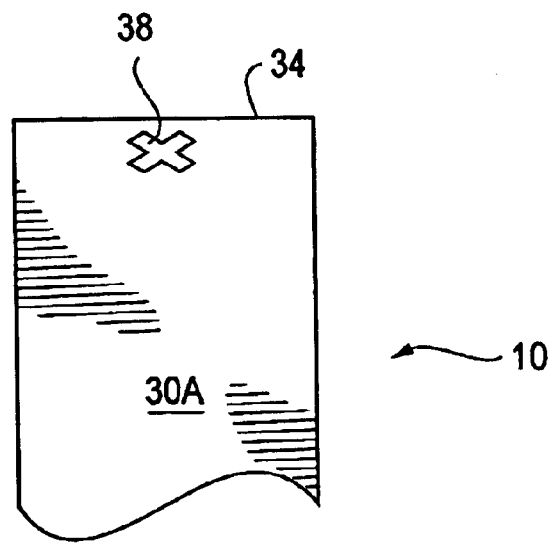
FIGS. 5A and B are partial top views of a coverslip, illustrating additional protuberance configurations.
Figure 5B:
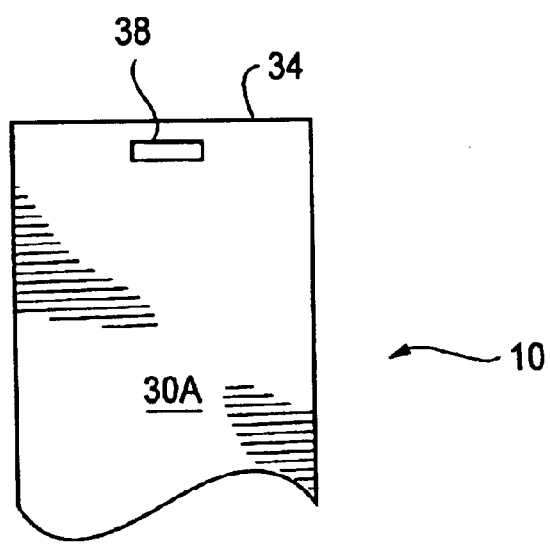

The glass coverslip 10 further includes at least one protuberance, generally designated 38, applied to, or mounted on, the top surface 30A, near the periphery 32. In this preferred embodiment, the protuberance 38 is a raised dot 40, centrally located adjacent the opposed end 34 of the glass plate 28. As shown in FIGS. 5A and B, the protuberance 38 may be in the form of an "X" or a bar.

Referring again to FIG. 1, the raised dot 40 provides an elevational alternation, generally designated 42, to the substantially planar top surface 30A of the glass plate 28. This alteration 42 defines a supporting plane 44 that is acutely oriented with respect to the planar top surface 30A. As used herein, the term "acutely oriented" and obvious modifications thereof mean an angle of 0 to 3 degrees. In this preferred embodiment, the supporting plane 44 is further defined by the glass plate 28, or more particularly the opposed end 36 thereof, as the adjacent coverslip 10 rests upon the glass plate 28, at one end, and upon the raised dot 40, at the other end.

Figure 3:
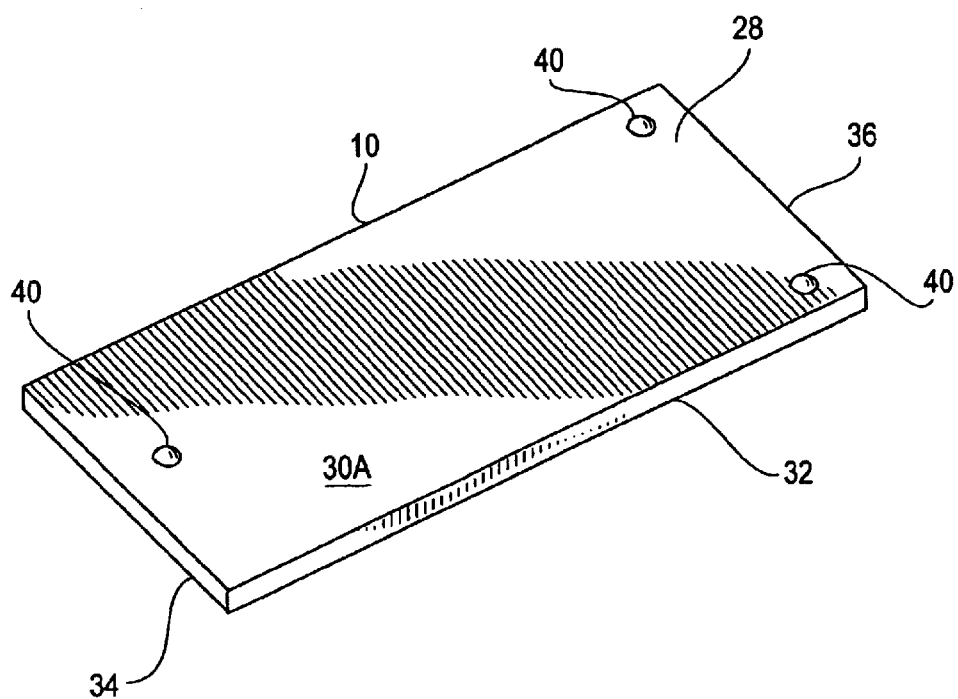
FIG. 3 is a perspective view of a second preferred embodiment.

In the preferred embodiment shown in FIG. 3, there are three protuberances 38 in the form of raised dots 40—one centrally located along the end 34 and two at the edges of the other end 36. The supporting plane 44, as defined by the three raised dots 40, is substantially parallel to the top surface 30A of the glass plate 28.

Figure 4:
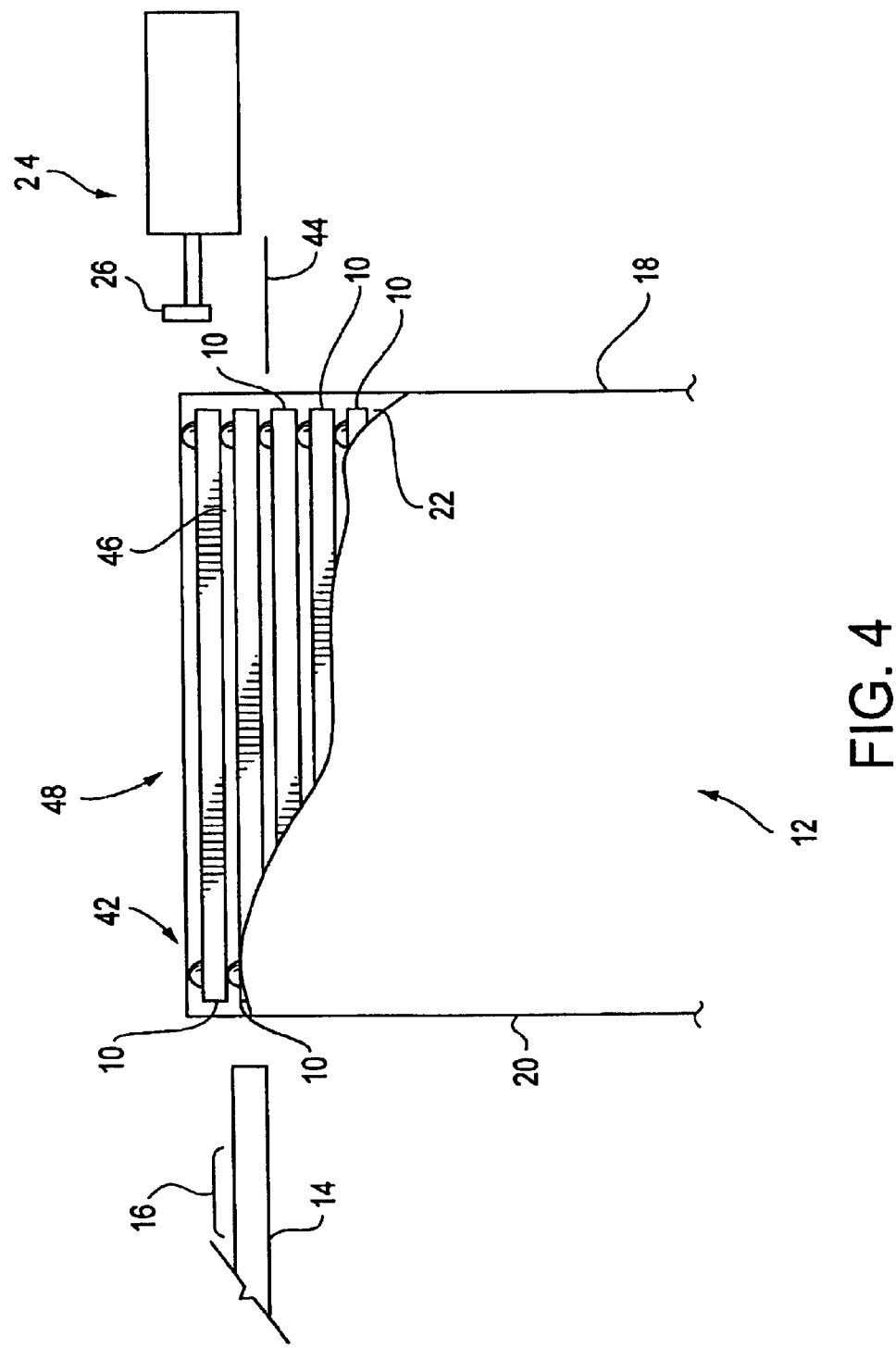
FIG. 4 illustrates the coverslipper apparatus of FIG. 1 with the second preferred embodiment shown in FIG. 3.

The supporting plane 44 establishes a gap 46 between vertically adjacent coverslips 10 in the magazine 18. The upper coverslip 10 rests along the supporting plane 44, substantially reducing the surface contact between the adjacently stacked coverslips 10 and substantially reducing adherence or sticking therebetween. The gap 46 further increases airflow, thereby reducing the possibility of condensation. With respect to the preferred embodiment shown in of FIGS. 1 and 2, the gap 46 is tapered; in the preferred embodiment of FIGS. 3 and 4, adjacent coverslips 10 are substantially parallel, such that the gap 46 is not tapered.

The protuberance 38, whether the dot 40 or an "X" or a bar, is preferably a curable compound, having a flowable state and a cured state. In one preferred embodiment, the dot 40 is a teflon paint which dries, or cures, in air. Once dried, the dot 40 has a substantially semi-circular shape, providing an elevational alteration 42 preferably in the range of 0.0005 to 0.005 inches. (In the FIGS. 1–4, the height of the protuberance 38 is exaggerated for clarity.)

With reference again to FIG. 1, alternating the pattern of the glass coverslips 10 in the magazine 18, such that the singular raised dot 40 of every other coverslip 10 is at the dispensing end 20 thereof, substantially avoids skewing. That is, the stacked coverslips 10 maintain a substantially vertical profile.

The various preferred embodiments of the coverslip 10 are readily packaged as a kit, generally designated 48. The kit 48 facilitates shipping and handling and readily drops into the magazine 18.

Figure 6:
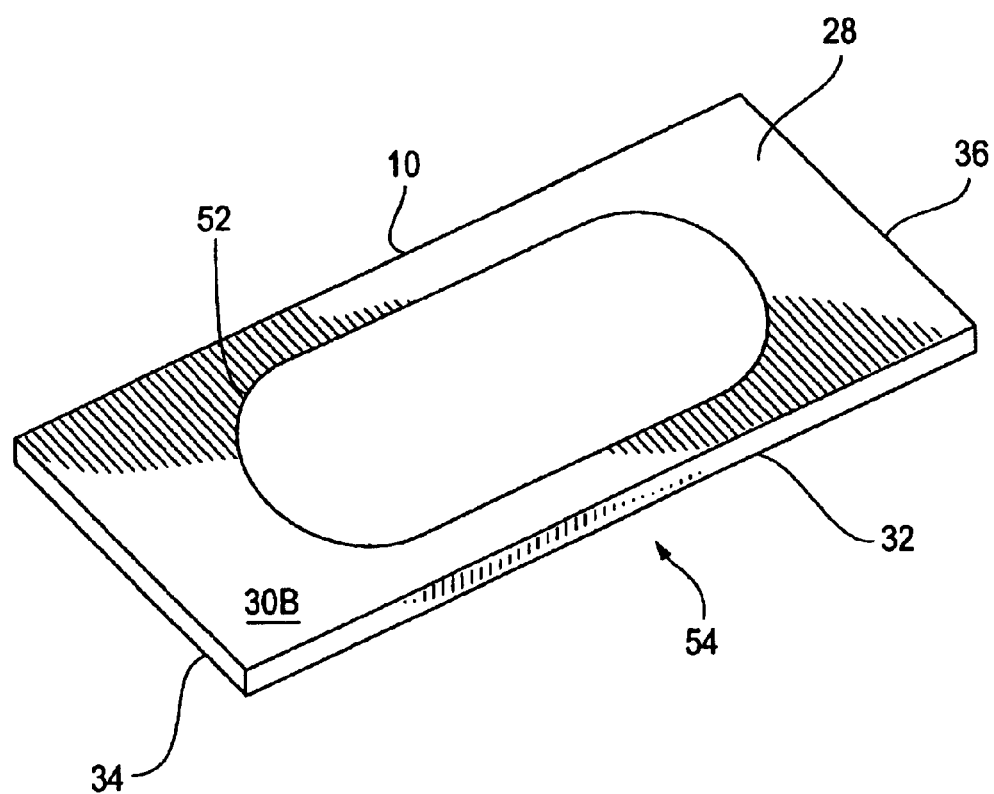
FIG. 6 is a perspective bottom view of the coverslip shown in FIG. 2.

With reference now to FIG. 6, the stackable non-stick coverslip 10 has an adhesive 52 applied to a central region, generally designated 54, of the bottom surface 30B. The adhesive 52 is preferably a liquid that dries, upon application to the coverslip 10, to a tackless or only slightly tacky state. The adhesive 52 is activated or partially dissolved by a solvent, prior to placement onto the glass slide 14 by the coverslipper 12. More particularly, the coverslipper 12 includes a dispensing system, generally designated 56, to apply the solvent to the bottom surface 30B of the coverslip 10 as it is "pushed" out of the magazine 18 and onto the glass side 14. Alternatively, the dispensing system 56 may apply the solvent directly onto the glass slide 14. In another embodiment, the solvent is applied manually.

As the activated adhesive 52 again dries, the coverslip 10 is affixed or bonded to the top surface 58 of the glass slide 12. The glass slide 12 can then stored for future analysis and study or as a permanent record of the analysis preformed.

The adhesive 52 is preferably oil-based or water-insoluble, such that the solvent is non-aqueous, i.e., hydrophobic or lipophilic. Acrylic copolymers such as Acryloid® A-21, commercially available from Rohm and Haas, Philadelphia, Pa., are suitable. Other suitable adhesives include olefin-based materials, e.g., vinyl and acrylate based polymers; cellulose acetates; cyanoacrylates; silicone-containing materials including silane- and siloxane-terminated monomer based polymers; polytetrafluoroethylene based adhesives; and hydrocarbon based polymers. Suitable solvents to render the adhesive 52 tacky include aromatic hydrocarbons such as toluene, xylene, and benzene; silicones such as dimethicones, cyclomethicones and substituted siloxanes; aromatic and aliphatic hydrocarbons; alkyl esters; benzyl or alkyl benzoates; alkyl, alkoxyalkyl and glyceryl esters; and mixtures thereof. While an oil-based or water-insoluble solvent is preferred, a water-based solvent, such as Shur/Mount Liquid Mounting Medium (VWR Cat. No. 15148-062), may be utilized with certain stains.

The present invention substantially avoids the difficult task of maintaining an adhesive within the automated coverslipper 12. The equally difficult task of pumping an adhesive through the automated coverslipper 12 is also avoided.

Various preferred embodiments of the present invention have been described herein. It is to be understood that modifications and changes can be made without departing from the true scope and spirit of the present invention, as defined by the following claims which are to be interpreted in view of the foregoing.

We claim:

1. A coverslip comprising, in combination:
   a glass plate having a substantially planar top surface and a substantially planar bottom surface;
   at least one protuberance on said substantially planar top surface, said protuberance providing an elevational alternation to said substantially planar top surface, said elevational alternation defining a supporting plane acutely oriented with respect to said substantially planar top surface; and
   a solvent-activated adhesive on said substantially planar bottom surface covering substantially all of the bottom surface.

2. A coverslip as claimed in claim 1 wherein said protuberance is a curable compound deposited on said substantially planar top surface.

3. A coverslip as claimed in claim 1 wherein said protuberance is a paint.

4. A coverslip as claimed in claim 1 wherein said protuberance is a raised dot of a curable compound deposited on said substantially planar top surface in a substantially semi-circular configuration.

5. A coverslip as claimed in claim 4 wherein said curable compound has a flowable state and a cured stated, said curable compound being deposited on the said substantially planar top surface in said flowable state and thereafter curing to said cured state.

6. A coverslip as claimed in claim 5 wherein said curable compound is a paint.

7. A coverslip as claimed in claim 1 or 2 wherein said solvent-activated adhesive is oil-based or water-insoluble.

8. A kit comprising, in combination:

plurality of coverslips stacked in an alternating pattern;

each of said stacked coverslips including:

a glass plate having top and bottom surfaces;

at least one protuberance on said top surface, said protuberance providing an elevational alternation to said top surface, said elevational alternation defining a supporting plane, acutely oriented with respect to said top surface, for an immediately adjacent one of said stacked coverslips, said supporting plane substantially minimizing surface contact between said adjacently stacked coverslips to substantially avoid adherence therebetween; and a solvent-activated adhesive on said bottom surface covering substantially all of the bottom surface.

9. A kit as claimed in claim 8 wherein said protuberance is a raised dot of a compound deposited on said top surface in a substantially semi-circular configuration.

10. A kit as claimed in claim 9 wherein said compound has a flowable state and a cured stated, said compound being deposited on the said top surface in said flowable state and thereafter hardening to said cured state.

11. A kit as claimed in claim 10 wherein said compound is a paint.

12. A kit as claimed in claim 8 or 10 wherein said solvent-activated adhesive is oil-based or water-insoluble.

\* \* \* \* \*